United States Patent [19]

Anhäuser

[11] Patent Number: 5,091,035
[45] Date of Patent: Feb. 25, 1992

[54] REMOVAL AID AND USE THEREOF

[75] Inventor: Dieter Anhäuser, Melsbach, Fed. Rep. of Germany

[73] Assignee: LTS Lohmann Therapie-Systeme GmbH & Co. KG, Neuwied, Fed. Rep. of Germany

[21] Appl. No.: 610,447

[22] Filed: Nov. 8, 1990

Related U.S. Application Data

[63] Continuation of Ser. No. 276,047, filed as PCT/DE88/00181, Mar. 22, 1988, abandoned.

[30] Foreign Application Priority Data

Apr. 3, 1987 [DE] Fed. Rep. of Germany ....... 3711256

[51] Int. Cl.⁵ ............................................. B65D 73/00
[52] U.S. Cl. ................................... 156/344; 156/256; 206/531; 206/601; 206/820; 428/43
[58] Field of Search ................ 206/531, 532, 530, 828

[56] References Cited

U.S. PATENT DOCUMENTS

| | | | |
|---|---|---|---|
| 3,230,649 | 1/1966 | Karn | 428/40 X |
| 3,501,365 | 3/1970 | Marshall | 156/283 X |
| 4,210,688 | 7/1980 | Sato | 156/256 X |

Primary Examiner—David A. Simmons
Assistant Examiner—James J. Engel, Jr.
Attorney, Agent, or Firm—Kalish & Gilster

[57] ABSTRACT

The invention relates to a removal aid for mechanically detachable substrates adhering to a sheet-like, flexible carrier material and in the form of cuts or predetermined breaking lines in said carrier material. At least in the contact surface of the carrier material is provided for each substrate a separate, non-linear cutting or predetermined breaking line, so that when pressure is exerted on the carrier material with a force component in a direction at right angles to the substrate contact surface a carrier material portion with the substrate portion adhering thereto and bounded by the cutting or predetermined breaking line can be bent in the direction of the substrate or substrates, so that at least part of the substrate in the border area thereof adjacent to the cutting or predetermined breaking line is detached from the carrier material and consequently a gripping portion is formed on the substrate for the complete removal of the latter.

13 Claims, 4 Drawing Sheets

REMOVAL AID AND USE THEREOF

This is a continuation of application Ser. No. 276,047, filed as PCT/DE88/00181, Mar. 22, 1988, now abandoned.

BACKGROUND AND SUMMARY OF THE INVENTION

The invention relates to a removal aid according to the preamble of claim 1 and the use thereof.

The invention more particularly relates to the separation of two materials adhering to one another, whereof one material is sheet or film-like and which are superimposed in the vicinity of a contact surface, such as is e.g. the case with plasters or labels, which are supplied with protective films for contact adhesive layers.

Hereinafter, the surfaces of the carrier material and the substrate are referred to as contact surfaces, which are portions of a carrier material or substrate surface. In addition, the term "substrate" is used both for substrate portions and parts and for the substrate itself.

Therefore the present invention relates to all combinations having a substrate/covering film combination at least as a subcombination.

The detachment or peeling off of a covering material layer or a covering film from a substrate e.g. having an adhesive layer in particular causes problems if the substrate is less flexible or roughly as flexible as the covering film and more especially if the substrate surface covered by the covering film and which is unprotected following the peeling off thereof has to be protected against contamination or damage during the removal of the peel-off film. A reason for protecting the substrate contact surface by a covering film can be e.g. the maintaining of its natural tackiness, its sensitivity to mechanical damage, or the sealing thereof e.g. against the escape of volatile components of the substrate. Conventionally the carrier material, usually a film, adheres by adhesive forces to the substrate, which can be overcome by removal.

The detachment of the carrier material is often problematical and leads to damage to the substrate contact surface to be protected if e.g. by means of a fingernail, knife or other instrument an attempt is made to remove from the substrate the carrier material parts remaining thereon. This procedure is in particular unsuccessful if the ratio of the rigidity of the substrate to the carrier material is unfavourable, e.g. if the carrier material is much more flexible than the substrate and also tears easily, or if a very soft substrate contact surface is to be protected.

This procedure is in particular impossible if it is necessary to avoid damage to the substrate contact surface through contact, e.g. in the case of sterile surfaces of bandages, the control layers of therapeutic plasters (e.g. of the type used for transfer of medicament active substances by skin contact) or surfaces having reactive materials.

For solving this problem it has already been proposed to provide linear cuts or predetermined breaking lines in the carrier material, whereby by removing or bending the carrier material it is possible to detach carrier material portions from the substrate.

However, hitherto by means of these known solutions it has not been possible to obtain a complete and easy exposure of the substrate, particularly if it is a relatively inflexible, sensitive substrate, such as a therapeutic plaster or e.g. a shaped plastic part and a very flexible carrier film, such as a thin aluminium foil or laminate or a polymer film. Particularly in the case of small substrate surfaces, it is difficult to completely expose them. The selective removal of individual substrate portions from a carrier material is also problematical.

The provision of curved cuts or predetermined breaking lines in the carrier film was described in U.S. Pat. No. 3,230,649 and on bending the material leads to the formation of a gripping portion for a part of the carrier material. However, the residue (13) still has to be removed by means of the fingernail or an auxiliary tool from the substrate. As yet no satisfactory process has been provided for the complete undamaged removal of the substrate from the carrier material. In the case of several substrate portions on the same carrier material, it is also possible for a type of peel-off band to interconnect the surfaces of several substrate portions, so that by pulling on a projecting part of the band, the substrate portions linked by it can be drawn off in a single operation from the carrier material. However, prior to the use of the substrate portions they must be separated from the peel-off band. Apart from the relatively complicated manufacture of this known arrangement, it only makes it possible to simultaneously detach several substrate portions and is restricted to small substrate portions. The insertion of strips or threads between the carrier material and substrate, said strips or threads projecting beyond the edge of the substrate portions, also represents an aid for detaching the substrate portions, but involves complicated technology.

All these proposals fail to bring about a satisfactory, problem-free detachment of the substrate from the carrier whilst to a minimum extent in paring the substrate, or otherwise complicated measures are required such as the provision of gripping strips.

The problem of the present invention is therefore to provide an aid for the removal of substrates from the carrier material not suffering from the disadvantage of the prior art. This problem is surprisingly solved by the features of claim 1. Advantageous further developments of the inventive principle can be gathered from the subclaims.

Due to the fact that, according to the invention, in each carrier material contact portion there is a separate, non-linear cutting or predetermined breaking line (i.e. line of weakness), when pressure is applied to the free carrier material surface in the vicinity of the contact surface it is possible to bend a part of the substrate from the contact surface plane, so that a substrate gripping portion is detached for the complete removal of the substrate. This permits a complete detachment or peeling-off of the substrate.

The carrier material and/or substrate can be in the form of more than one layer and different materials and if e.g. the substrate is a therapeutic plaster, the substrate contact surface layer need not be made from the same material throughout.

The materials usable for this purpose must be flexible in the case of the carrier material, whereas in the case of the substrate they can also be rigid. Thus, the substrate can be constituted by shaped plastic members, such as "self-adhering" emblems, Coats of Arm, etc. After removing the substrate from the carrier material a substrate layer surface is freed, which can e.g. be finished in contact adhesive manner and/or which is also permeable to active substances, such as medicaments, such as e.g. the skin contact layer of therapeutic plasters which does not necessarily have to be contact adhesive. In the latter case the carrier material serves as a barrier, which prevents the undesired diffusing of active substances out of a flat therapeutic system. It is also not necessary for the contact surface to be planar and can be shaped in accordance with the intended use of the substrate.

The production of predetermined breaking or cutting lines (lines of weakness) in the carrier material takes place by per se known processes and e.g. for producing cuts punching, cutting, squeezing or stamping the carrier material is preferred. However, it is also possible to cut by laser or high frequency. Predetermined breaking lines can also be produced by punching, perforating, local chemical or heat treatment and particularly in the case of polymer carrier materials by laser cutting etc., as is known to the relevant Expert. The lines can obviously be produced before or after applying the substrate or substrates.

The invention is described in greater detail hereinafter relative to non-limitative embodiments and the attached drawings, wherein show:

DESCRIPTION OF PREFERRED EMBODIMENTS

Figure 1:
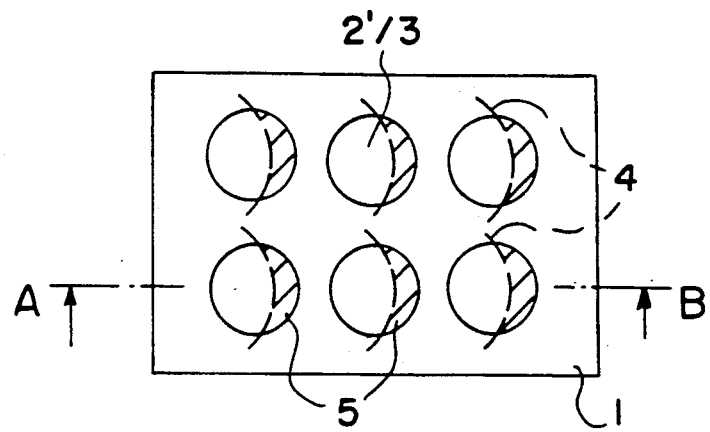
FIG. 1 a plan view of the carrier material side of an inventive substrate/carrier material combination with round substrates.

FIG. 1 diagrammatically shows an embodiment of an inventive combination of substrate 2 and carrier material 1, six round substrates 2 being arranged on a thin carrier material 1. The substrates 2 here comprise a useful layer 2', such as e.g. a polymer film, if the substrate is a label. However, it can also be a complicated constructed therapeutic plaster, with e.g. a covering layer, active substance reservoir, as well as optionally further supporting and/or control layers and a contact adhesive layer 3.

The carrier material 1 projects on all sides over the contact surfaces of substrates 2. In the contact surfaces within the carrier material 1 curved lines of cut 4 are provided, which intersect the edges of the contact surface. The gripping portions 5 of the substrate having the same or a lower flexibility than the carrier material are raised during the removal process by pressure on the free surface of carrier material 1 and can then serve as gripping portions 5.

Figure 2:
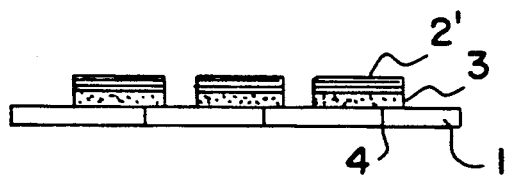
FIG. 2 a cross-section through the combination of FIG. 1 along line A-B.

FIG. 2 shows a cross-section along line A-B of FIG. 1. It is possible to see in carrier material 1 the arrangement of cuts 4, which are located in the area of the contact surface between the substrate 2 comprising a substrate useful layer 2' and a contact adhesive layer 3 and the carrier material 1. Cut 4 is so far from the substrate edge that on peeling off a gripping portion 5 (FIG. 5) sufficiently large for removing the complete substrate 2 is formed.

Figure 3:
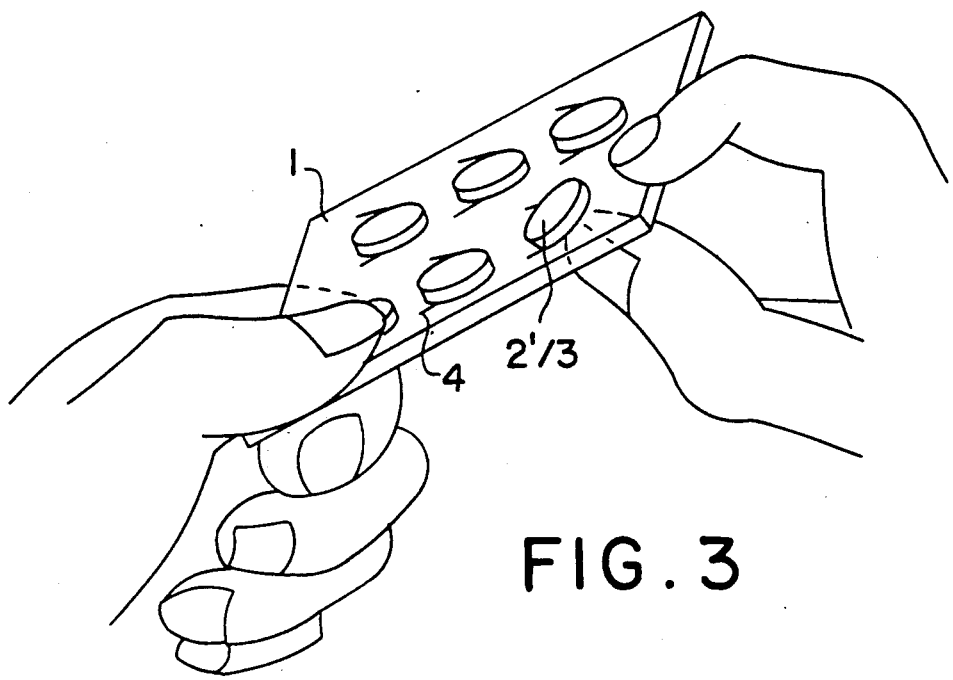
FIG. 3 the handling operation on detaching a substrate from the combination according to FIG. 1.
Figure 4:
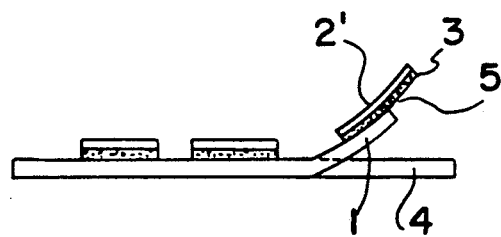
FIG. 4 the detachment of a substrate portion, as shown in FIG. 3 in a cross-sectional view.

FIG. 3 is a perspective view of the use of the inventive removal aid, whereby on using finger pressure the gripping portion 5 of a substrate can be exposed. The carrier material 1 is here held with one hand, whilst the thumb of the other hand forces upwards from below a portion of the carrier material contact surface. As shown in the cross-sectional representation of FIG. 4, the gripping portion 5 is detached from the carrier material 1. In FIGS. 3 and 4 the cuts in the carrier material are designated 4.

Figure 5:
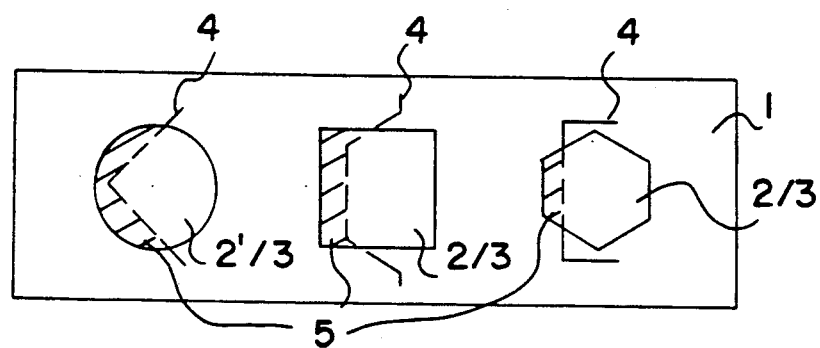
FIG. 5 a plan view of a further inventive substrate/carrier material combination with cutting or predetermined breaking lines according to the invention with different substrates having different geometrical configurations.

Another preferred embodiment of the invention is shown in FIG. 5. Substrates 2 with a circular, square and hexagonal shape adhere to the carrier material 1 and for the removal thereof cuts 4 are provided in angular manner. Thus, the cut can represent two sides of a triangle, three sides of a trapezium, three sides of a polygon or portions of a polygon. The gripping portions resulting from the removal process are once again designated by 5.

Figure 6:
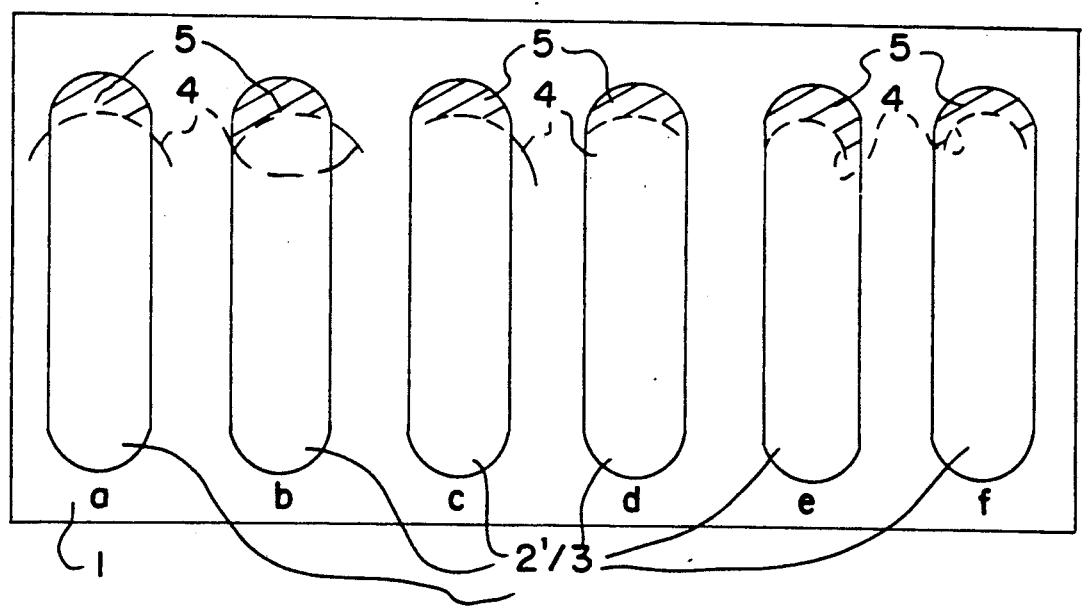
FIG. 6 a plan view of a further inventive substrate/carrier material combination with oval-elongated substrates with different cutting line configurations.

FIG. 6 makes it clear that the invention also applies to substrates 2 with widely differing dimensions. There are five substrates 2 with various possible cutting line configurations:

a: the cutting line intersects the edge of the contact surface on two sides;
b: the cutting line contacts a contact surface edge and intersects another contact surface edge;
c: the cutting line ends on one side inside and on the other side outside the contact surface;
d: the contact line is in contact by its ends with two contact surface edges;
e: one end of the cutting line contacts the contact surface edge, whilst the other end is located within the contact surface;
f: both cutting line ends are within the contact surface.

In all these cases by exerting pressure on the free surface of the carrier material 1 an adequate gripping portion 5 of the substrate 2 can be exposed.

Figure 7:
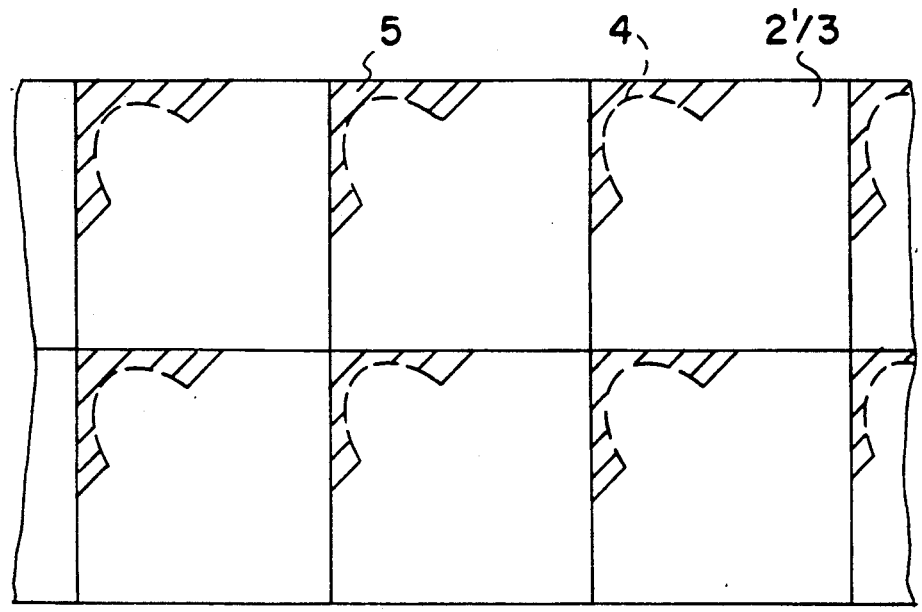
FIG. 7 a plan view of another inventive substrate/carrier combination, in which the carrier material and substrate substantially have the same surface area.

An example of another preferred embodiment is shown in FIG. 7. This is a plan view of part of a band-like arrangement, in which the overall substrate surface subdivided by engaging quadratic substrate portions 2 and which are only separated by lines of cut is identical with the surface of carrier material 1. Through a curved cut 4 in the not visible carrier material 1 in each case one corner of each substrate portion, the possibility exists with the aid of the gripping portions 5 which can be exposed by pressure on the underside of the arrangement of removing any random substrate 2 independently of the remaining substrates 2.

Figure 8:
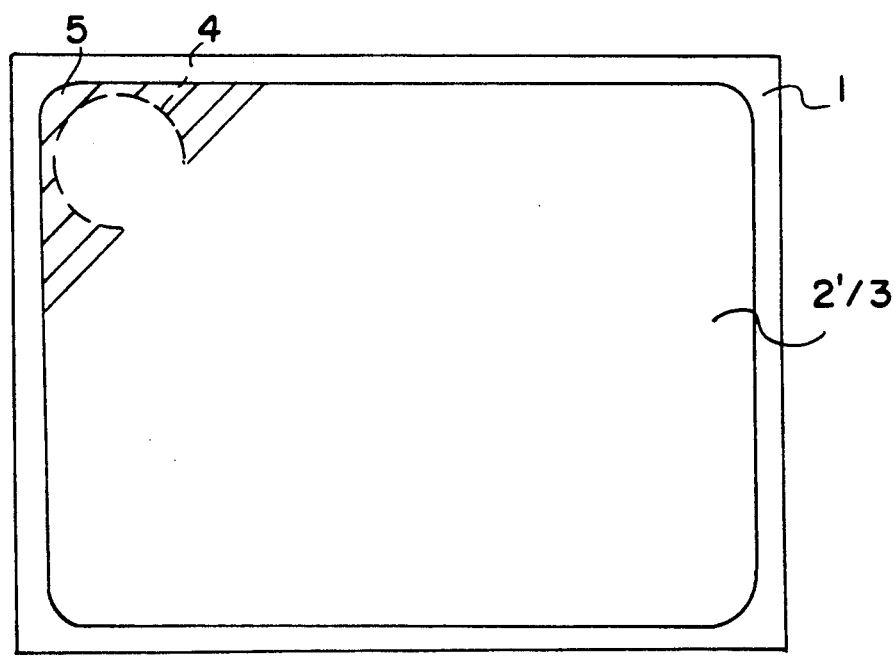
FIG. 8 a plan view of a substrate/carrier combination with a large substrate/carrier material contact surface.

FIG. 8 finally illustrates the usability of the invention for large substrates. In plan view it is possible to see the substantially rectangular substrate 2 with rounded corners, which adheres to a somewhat larger area carrier material 1. A curved cutting line 4 is provided in the carrier material in one corner of the contact surface and the two ends of the line are located within said contact surface. Here again, by pressure on the underside of the carrier material in the vicinity of the cut, it is possible to remove the gripping portion 5 from said carrier material.

The embodiments illustrated in the description and shown in the drawings make it clear that the invention offers a very broad spectrum of use and that considerable advantages are obtained during the handling of substrates with covering materials.

I claim:

1. A therapeutic system for transfer of a medicament active substance by skin contact comprising at least one manually detachable therapeutic plaster substrate containing a medicament active substance, said substrate adhering to a sheet-like, flexible carrier material having a contact surface contacting the substrate in the form of predetermined lines of weakness in said carrier material, characterized in that a separate, non-linear, predetermined line of weakness (4) is provided for each said substrate at least in the contact surface of carrier material (1) substantially beneath each said substrate in such a way that when pressure is applied to the carrier material (1) with a force component in a direction at right angles to a corresponding substrate contact surface, it is possible to bend a carrier material portion bounded by the predetermined line of weakness (4) with the substrate portion adhering to it in the direction of the substrate or substrates (2), so that at least part of substrate (2) is detached in its border area adjacent to the predetermined line of weakness (4) from the carrier material (1) and consequently a gripping portion (5) is formed on the substrate for the complete removal of the latter.

2. Therapeutic system according to claim 1, characterized in that the surface of the carrier material (1) is larger than the substrate or substrates (2).

3. Therapeutic system according to one of the claims 1 or 2, characterized in that the predetermined line of weakness (4) is located entirely within the contact surface of the carrier material (1).

4. Therapeutic system according to one of the claims 1 or 2, characterized in that the predetermined line of weakness (4) interconnects two edges of the contact surface of carrier material (1).

5. Therapeutic system according to one of the claims 1 or 2, characterized in that the predetermined line of weakness (4) passes beyond at least one edge of the contact surface of the carrier material.

6. Therapeutic system according to claims 1 or 2, characterized in that the substrate (2) is sheet-like.

7. Therapeutic system according to claims 1 or 2, characterized in that the carrier material (1) is in multilayer form.

8. Therapeutic system according to claims 1 or 2, characterized in that the substrate (2) is in multilayer form.

9. Therapeutic system according to claims 1 or 2, characterized in that the carrier film (1) is more flexible than the substrate (2).

10. Therapeutic system according to claim 1, wherein the lines of weakness comprise cuts.

11. A therapeutic system according to claim 1, characterized in that the carrier material and the substrate are of substantially equal flexibility.

12. A therapeutic system according to claim 1 characterized in that the carrier material is more flexible than the substrate.

13. A therapeutic system according to claim 1, characterized in that the carrier material is less flexible than the substrate.

* * * * *

UNITED STATES PATENT AND TRADEMARK OFFICE
CERTIFICATE OF CORRECTION

PATENT NO. : 5,091,035
DATED : February 25, 1992
INVENTOR(S) : D. Anhauser

It is certified that error appears in the above-identified patent and that said Letters Patent is hereby corrected as shown below:

On the Title page, item [54]

In the title, replace "Removal Aid and Use Thereof" with

--THERAPEUTIC SYSTEM--.

Signed and Sealed this

Twenty-fifth Day of May, 1993

Attest:

MICHAEL K. KIRK

*Attesting Officer*     *Acting Commissioner of Patents and Trademarks*